US005702912A

United States Patent [19]

Hemker et al.

[11] Patent Number: 5,702,912
[45] Date of Patent: Dec. 30, 1997

[54] METHOD TO DETERMINE THE CONCENTRATION OF ANTICOAGULANTS

[75] Inventors: Hendrick Coenraad Hemker, Maastricht; Robert Johan Wagenvoord, Eysden, both of Netherlands; Hans-Jurgen Kolde, Ottobrunn, Germany

[73] Assignee: Dade International Inc., Deerfield, Ill.

[21] Appl. No.: 564,986

[22] Filed: Nov. 30, 1995

Related U.S. Application Data

[63] Continuation of Ser. No. 160,469, Dec. 1, 1993, abandoned, which is a continuation of Ser. No. 899,226, Jun. 16, 1992, abandoned, which is a continuation of Ser. No. 609,340, Nov. 5, 1990, abandoned.

[51] Int. Cl.[6] .............................. C12Q 1/56; G01N 33/86
[52] U.S. Cl. ........................... 435/13; 435/214; 436/69
[58] Field of Search .......................... 435/13, 23, 214; 422/61; 436/69, 164

[56] References Cited

U.S. PATENT DOCUMENTS

| | | | |
|---|---|---|---|
| 4,234,682 | 11/1980 | Bartl | 435/13 |
| 4,409,327 | 10/1983 | Bartl | 435/13 |
| 4,473,639 | 9/1984 | Sommer | 435/13 |
| 4,851,336 | 7/1989 | Yin | 435/13 |

FOREIGN PATENT DOCUMENTS

| | | | |
|---|---|---|---|
| 0049877 | 4/1982 | European Pat. Off. | C12Q 1/56 |
| 0229234 | 7/1987 | European Pat. Off. | C12Q 1/56 |
| 0406971 | 1/1991 | European Pat. Off. | C12Q 1/56 |
| 0420332 | 4/1991 | European Pat. Off. | C12Q 1/56 |

OTHER PUBLICATIONS

Teien, Assay of Heparin in Plasma . . . , Pergamon Press, 8:413–6 1976.
Wagner II, A New Assay for Determination of Heparin . . . , Fibrinolysis 4 (Supp. 1) 26 1990.
Buchanan et al., The Relative Importance of Thrombin Inhibition and Factor Xa Inhibition to the Antithrombotic Effects of Heparin, Blood 65:198–201 (Jan. 1985).
Fickenscher et al. II, Poster at the German 9th Congress of Thrombosis and Haemostasis; Feb. 22–25, 1989, Bremen Germany.
Pieters et al., The Limited Importance of Factor Xa Inhibition to the Anticoagulant Property of Heparin in Thromboplastin–Activated Plasma, Blood 72:2048–52 (Dec. 1988).
Pizzulli et al., Inhibition of the Heparin Action by Glycerol Trinitrate, Deuth. Med. Wachr, 113: 1837–40 (1988).
Teien et al., Assay of Heparin in Plasma using a Chromogenic Substrate for Activated Factor X, Pergamon Press, Inc. 8:413–16 (1976).
Wagner et al. I,A New Assay for Determination of Heparin in Plasma using a Chromogenic Substrate; Poster, 11th International Congress on Thrombosis, Jun. 24–28, 1990, Ljubljana, Yugoslovia.
Witt, New Methods of Coagulation Analysis using Chromogenic Substrates, J. Clin. Chem. Clin. Biochem. 15:239–44 (1977). Abstract Only.
Wagner et al. II, A New Assay for Determination of Heparin in Plasma using a Chromogenic Substrate, Fibrinolysis 4 (Supp. 1): 26 (1990).

*Primary Examiner*—Ralph Gitomer
*Attorney, Agent, or Firm*—Cynthia G. Tymeson

[57] ABSTRACT

The present invention relates to a method to determine the concentration of anticoagulants as a function of the inhibition of thrombin formation in an assay mixture. The assay mixture is composed of two reagents and the diluted plasma sample. The diluted plasma sample containing an anticoagulatory substance is mixed with a clotting factor reagent, which is a combination of an excess amount of purified coagulation factors of the endogenous system, phospholipids and a weak thrombin inhibitor, which can be potentiated by an anticoagulatory substance. Then a coagulation cascade activator and calcium chloride, an activator reagent, is added to the mixture and formed thrombin is measured after a chosen incubation time. A proportionality between the inhibition of the thrombin formation and the anticoagulatory active components allows for a determination of the concentration of anticoagulatory active components in the sample.

13 Claims, 8 Drawing Sheets

Fig. 1

Fig. 3 Standard Curve for Hirudin

METHOD TO DETERMINE THE CONCENTRATION OF ANTICOAGULANTS

This is a continuation of application Ser. No. 08/160,469, filed Dec. 1, 1993 now abandoned, which is a continuation of Ser. No. 07/899,226 filed on Jun. 16, 1992, now abandoned, which is a continuation of Ser. No. 07/609,340 filed on Nov. 5, 1990, now abandoned.

FIELD OF THE INVENTION

This invention relates to a method to determine the concentration of an anticoagulant in a sample.

BACKGROUND OF THE INVENTION

Anticoagulants are used in the clinic to protect patients from thrombosis, i.e. the formation or presence of a clot in a blood vessel. The most frequently used anticoagulants are acetylsalicylic acid (aspirin), coumarin derivatives and heparin.

Thrombin catalyses the formation of fibrin from fibrinogen; thus, thrombin activity is responsible for the coagulation of blood or plasma. Blood or plasma contain antithrombin III, which is a relatively weak inhibitor of thrombin. However, by binding heparin to antithrombin III, it becomes a very potent inhibitor of the proteolytic activity of thrombin. Consequently, heparin is often administered to patients with risk of thrombosis. A precise adjustment of the heparin concentration is extremely important. If the dose of heparin is too low there is the danger of thrombosis or embolism and on the other hand if the dose is too high bleeding can result. For this reason the concentration of anticoagulatory substances in patient's plasma determines the administration of an anticoagulatory substance.

A number of methods have been developed to determine the concentration of anticoagulatory substances in plasma. One method involves determining the clotting activity of blood or plasma. In particular, the activated partial thromboplastin time and the thrombin time are determined. These methods, however, depend on the activity of coagulation factors and are additionally influenced by the presence of fibrin degradation products. Fibrin degradation products have an anticoagulant action for two reasons. Firstly, fragment E has an antithrombin effect and thus causes prolongation of the thrombin time. Secondly, some fragments of fibrinogen can polymerize and, thus, delay or prevent fibrin clot formation. Additionally, the activated partial thromboplastin time measurements are influenced by glycerol trinitrate, which is administered in combination with heparin. Pizzuli et al., *Hemmung der Heparinwirkung durch Glyceroltrinitrat (Inhibition of the action of heparin by glycerol trinitrate)*, Dtsch. Med. Wschr. 113, 1837 (1988). Moreover, it has been observed that these methods are not very precise, particularly in situations of low or high concentration of heparin. Thromb. Res. 8, 413 (1976).

Other methods for determining the concentration of heparin in a plasma sample involve adding a proteolytic enzyme selected, from the group consisting of thrombin and factor $X_a$, adding a chromogenic substrate for the enzyme and measuring dye released from the chromogenic substrate. Because thrombin and factor $X_a$ are inactivated more rapidly by antithrombin III in the presence of heparin, the residual chromogenic activities of these enzymes are a function of the amount of heparin present. Bartl et al., U.S. Pat. Nos. 4,234,682 and 4,409,327; J. Clin. Chem. Clin. Biochem. 15, 239 (1977). These methods, however, similarly lack sensitivity for low concentration of heparin. Pieters et al., *The Limited Importance of Factor $X_a$ Inhibition to the Anticoagulant Property of Heparin in Thromboplastin-Activated Plasma*, Blood 72, 2048 (1988). Buchanan et al., *The Relative Importance of Thrombin Inhibition and Factor $X_a$ Inhibition to the Antithrombotic Effects of Heparin*, Blood 86, 198 (1985).

Still another method involves measuring the activity of heparin by incubating an excess of factor $X_a$ with plasma. After a defined incubation time, phospholipids, calcium ions and various plasma proteins are added and the coagulation time is determined. Yin E., Method and Compositions for Heparin Assays, EPA 0,217,768. However, it is disputed in the technical literature whether the determination of antifactor $X_a$ activity actually correlates with the clinical potency of heparin. Hemker H. C., Thrombosis and Haemostasis; Eds. Verstraete M. et al., Leuven University Press 1987, pp. 17–36.

For monitoring relatively small concentrations of standard heparin as well as of low-molecular weight heparins, glycosaminoglycans, dermatan sulphate and other inhibitors with anticoagulatory activity, processes are required, which can detect even the slightest amounts of active anticoagulatory substance with certainty. The problem of the present invention was to develop for these compounds a testing system which offers advantage both in respect to sensitivity and also specificity over the method of the state of the art.

SUMMARY OF THE INVENTION

According to the present invention the previously discussed object is achieved by using a combination of an excess amount (i.e., over the concentration in a patient's sample) of purified clotting factors of the endogenous system, a sufficient amount of calcium ions to stabilize clotting factors, a sufficient amount of phospholipids to catalyze the reaction and a weak thrombin inhibitor, e.g. antithrombin III. These reactants are incubated with a diluted plasma sample. A coagulation cascade activator, comprising Factor IXa and $CaCl_2$ is then added to the mixture. By the action of the cascade activator, trace amounts of thrombin are slowly formed. Thrombin formation at first is a very slow and ineffective process, since the cofactors factor V and factor VIII are present in a nonactive form. If the plasma sample, however, contains anticoagulatory active substances, then the weak thrombin inhibitor in the reaction mixture, i.e. antithrombin III, is potentiated by the anticoagulatory active substance and therewith the thrombin-dependent reactions are suppressed. This leads to the result that within a certain period of time less thrombin is formed. A proportionality between the inhibition of the thrombin formation and the anticoagulatory active components of the sample allows for a determination of the concentration of anticoagulatory active components in the sample. Many anticoagulants such as hirudin or synthetic inhibitors also directly inhibit thrombin, by passing the antithrombin III in the reagent mixture mentioned above. Therefore, antithrombin III can be omitted if these substances are assayed.

The invention relates to a method to determine the concentration of an anticoagulant in a sample as a function of the inhibition of thrombin formation in said sample comprising: adding a sufficient amount of buffer to dilute said sample; combining said sample with a sufficient amount of clotting factor reagent to suppress thrombin formation in said sample; adding a sufficient amount of activator reagent to initiate the coagulation cascade; adding a sufficient amount of buffered reagent that complexes with thrombin;

and, correlating thrombin concentration said sample with the known concentration of an anticoagulant to determine the concentration of said anticoagulant in said sample.

The above described method wherein said clotting factor reagent is comprised of a given amount of clotting factor greater than the concentration of the clotting factors present in a sample, a sufficient amount of calcium ions to stabilize said factors, a sufficient amount of phospholipids to catalyze the reaction; a sufficient amount of dextran sulfate to neutralize platelet factor 4 in the sample, and a sufficient amount of weak thrombin inhibitor to suppress thrombin formation in said sample. In the method described above, the anticoagulant is selected from the class consisting of: heparin, α-NAPAP and dermatan sulfate. Additionally, in the above described method the weak thrombin inhibitor is selected from the class consisting of antithrombin III, heparin cofactor II or a synthetic physiological inhibitor of thrombin, which is potentiated by an anticoagulant.

Additionally, this invention relates to a method wherein said clotting factor reagent is comprised of a given amount of clotting factor greater than the concentration of said clotting factors present in a sample, a sufficient amount of calcium ions to stabilize the factors, a sufficient amount of phospholipids to catalyze the reaction; a sufficient amount of dextran sulfate to neutralize platelet factor 4 in the sample. In the method described above the anticoagulant is selected from the class consisting of hirudin and synthetic or physiological inhibitors of thrombin.

Still additionally, this invention relates to test kits to practice the above described methods.

DETAILED DESCRIPTION OF THE INVENTION

The assay is based on the following principle. A mixture is prepared with purified clotting factors greater than the concentration of clotting factor normally present in a sample, a sufficient amount of calcium ions to stabilize said factors, a sufficient amount of phospholipids to catalyze the reaction; a sufficient amount of dextran sulfate to neutralize platelet factor 4 in the sample, and a sufficient amount of weak thrombin inhibitor to suppress thrombin formation in said sample. It should be noted that for anticoagulatory compounds like hirudin or synthetic thrombin inhibitors the weak inhibitor in the clotting factor reagent mixture can be omitted. To this clotting factor reagent mixture is added the diluted sample, containing either a thrombin inhibitor or an anticoagulatory compound, which potentiates the weak thrombin inhibitor in the mixture. Then an activated clotting factor and calcium ions are added to start the coagulation cascade, resulting in initially slow thrombin formation. The first traces of thrombin activate factors V and VIII. The activated factors V and VIII cause an enormous acceleration of the activation reactions and thus the rate of thrombin formation rapidly increases and clotting occurs, i.e. conversion of fibrinogen to fibrin. To convert fibrinogen, a high concentration of thrombin is necessary and this reaction is not started by the first small traces of thrombin which can activate factors V and VIII. Activated factors V and VIII may induce rapid formation of thrombin at high concentrations resulting in fibrin/clot formation.

These first traces of thrombin are inhibited only slightly by the weak thrombin inhibitor in the mixture, but much more by a fast acting thrombin inhibitor in the sample or by potentiating the weak thrombin inhibitor in the mixture. Inhibition of the initial slow thrombin formation causes a delay or prevention of the activation of factors V and VIII and thus the formation of large amounts of thrombin is postponed or prevented.

When antithrombin III is present in the reaction mixture only a small effect is noticed on thrombin formation, because it is a weak thrombin inhibitor. However, when antithrombin III is added to the mixture the system will become sensitive for heparins, because these compounds affect the potency of antithrombin III as thrombin inhibitor. The more heparin that is present the more potent antithrombin III will inhibit thrombin and thus the bulk formation of thrombin is delayed or even prevented in such a case.

When heparin cofactor II, which also is a weak thrombin inhibitor, is present in the mixture, the system will become sensitive for dermatan sulphate, because this compound makes heparin cofactor a better inhibitor for thrombin.

By the use of an excess amount of and standardized amounts of coagulation factors, antithrombin III, phospholipids and calcium ions with a simultaneous high dilution of the sample a high specificity and sensitivity for heparin or heparin-like anticoagulants is achieved. A high excess of coagulation factors means a concentration of several factors above the $K_M$. The $K_M$ is the so-called Michaelis constant (concentration) at which the enzymatic reaction rate is 50% of its highest possible rate. If such an excess concentration is used the reaction rate is close to its maximum and is not dependent on the coagulation factor concentration. In contrast to the earlier mentioned methods, which made use of the coagulation factors and inhibitors of the patient's plasma sample, the present method provides that all the required coagulation factors are used in high excess and constant concentration. For this reason in this measuring system accidental fluctuations of the activity of individual coagulation factors as well as the presence of fibrin splitting products and similar factors within the sample no longer play any role.

Coagulation factors were isolated from bovine blood according to known processes described in the literature (Factor X: Biochemistry 11, 4882 (1972); Factor VIII: Biochemistry 19, 401 (1980); Prothrombin: J. Biol. Chem. 249, 594 (1974); Factor V: J. Biol. Chem. 254, 508 (1979); Factor IX: Biochemistry 12, 4938 (1973); Antithrombin III: Br. J. Haematol. 233 (1975)). Factor $IX_a$ was prepared by activation of factor IX (Biochemistry 13, 4508 (1974)). It should be noted that not only bovine blood, but also the blood of other species, inter alia also human blood, is suited as source of coagulation factors or also recombinant coagulation factors. For the clotting factors the broad and preferred ranges are as follows: Factor X, broad range, 10–1000 nm, preferred range, 30 to 300 nm; Factor VIII, broad range, 0.35 to 2.5 nm, preferred range, 0.7 to 1.4 nm; Factor V, broad range 0.5–20 nm, preferred range, 1–2.5 nm; Prothrombin and antithrombin III, broad range, 20–1000 nm, preferred range, 60–400 nm. Heparin cofactor II are useful in the following ranges respectively: Heparin Cofactor II, broad range, 20–350 nm, preferred range, 140 nm.

Additionally, the clotting factor reagent contains a sufficient amount of $CaCl_2$ to stabilize the clotting factors. It has been found that the broad range of 50–100 µM, with a preferred amount of 100 µM $CaCl_2$.

For the production of phospholipid micelles purified phospholipids such as phosphatidylserine, phosphatidylcholine as well as cholesterol in various mixing ratios in a solution of chloroform were used. The individual phospholipids were mixed with one another in the desired weight ratio and the solvent was evaporated by a nitrogen stream. The concentration of the lipids is between 2 and 60 µM, preferably 9 µM. By ultrasound a stable suspension of the phospholipid was established and this was used as source of phospholipid vesicles. The ultrasound treatment time amounted to two hours. As molar ratio between the above-mentioned phospholipids there was used a relation of 23% phosphatidylserine, 69% phosphatidylcholine and 8% cholesterol. However, other ratios show satisfactory results. For phospholipids, the broad useful range to catalyze the reaction is 9–250 µM, but the preferred range is 20–50 µM.

Additionally, an inert protein such as albumin is added to clotting factor reagent to prevent the clotting factors from adhering to the reaction vessel. It has been found that the broad range of 2–20 mg/mL of inert protein, but preferably about 10–20 mg/mL of inert protein is used. Albumin is necessary to keep small amounts of protein, in solution. In the clotting factor reagent the concentrations of factors V and VIII are very low. When no carrier protein is added factors V and VIII and to a lower extent the other coagulation factors will bind to the vessel wall and thus become less active. To serve as carrier protein any inert protein is suitable, examples are serum albumin and ovalbumin.

Additionally, dextran sulphate is added to the clotting factor reagent to inhibit the influence of platelet factor 4 in the sample. It has also been observed that the broad useful range of dextran sulphate is 0.33–1.9 µg/mL, while the preferred amount is about 0.4–1 mg/ml. Dextran sulphate is necessary to neutralize platelet factor 4, which is released from blood platelets when they are activated. Platelet factor 4 neutralizes heparin and in cases when blood platelets are activated part or all of the present heparin might be neutralized. Dextran sulphate prevents this heparin neutralizing effect of platelet factor 4. Dextran sulphate does not interfere with the coagulation reactions below a concentration of 1.6 µg/ml. Any other compound that prevents heparin neutralization by platelet factor 4 can be used.

The activator reagent causes the start of the coagulation cascade, resulting in slow thrombin formation. The preferred activator is factor IXa, $CaCl_2$ and an inert protein. Factor IXa can be added in the range of 0.025–40 nM, but perferably about 1–5 nM. It should be noted that the coagulation cascade can be triggered by the addition of factor XIa or factor XIIa. In this situation, the clotting factor reagent must include factor IX or factor XI complex in concentration range of about 50 nM. The broad range of $CaCl_2$ that has been found to be useful is 5–40 mM, but between about 8–33 mM is preferred. The broad range of inert protein in the reagent is 0.4 to 20 mg/mL, but between 0.5–1 mg/mL is preferred.

The detection reagent includes a chromogenic, luminogenic, fluorogenic or electrogenic compound. If the detection reagent is chromogenic, the preferred reagent is S2238 (Kabi). The amount of this substrate reagent range from, 0.5 to 1 mm, but 0.5 mm is preferred. The substrate reagent also includes a calcium chelating agent like EDTA to prevent further thrombin generation. The broad range of the calcium chelating agent is in excess of the $CaCl_2$, but preferably equal or greater than 10 mM. The substrate reagent also includes a sufficient amount of an inert protein to prevent the clotting factors from adhering to the reaction vessel. The inert protein in this reagent broadly ranges from 0.4 to 20 mg/mL but between about 0.5–5 mg/mL is preferred.

A typical reagent from a chromogenic substrate determination of anticoagulants was prepared as follows (all solutions were made in 175 mM NaCl, 50 mM Tris-HCl, pH 7.9):

Clotting Factor Reagent:

30 nM factor X, 0.7 nM factor VIII, 1.4 nM factor V, 70 nM prothrombin, 70 nM antithrombin III, 9 µm phospholipids, 0.1 mM $CaCl_2$, 20 mg/ml albumin, 0.4 µg/ml dextran sulphate.

Activator Reagent:

1.6 nM factor $IX_a$, 15 mM $CaCl_2$, 0.5 mg/ml albumin.

Substrate Reagent:

0.5 mg/ml albumin, 36 mM EDTA, 0.875 mM substrate S2238™ (Kabi Vitrum Co.)

It should be noted that other chromogenic substrates for thrombin can also be used. The necessary concentration depends on the kinetic constants of the substrates.

The process can also be carried out as a coagulation test, however, by addition of fibrinogen. The fibrinogen may be human or bovine and is added in the range of 4–10 mg/mL, but perferably about 5 mg/mL. This variant is especially advantageous in the application of this method in whole blood. Furthermore, the thrombin formation rate can be used as end point.

The same process can also be used to measure other anticoagulatory active substances directed against thrombin or processes leading to thrombin formation, such as hirudin or synthetic protease inhibitors.

EXAMPLE 1

Determination of Unfractionated Heparin With the Chromogenic Substrate Method

Figure 1:
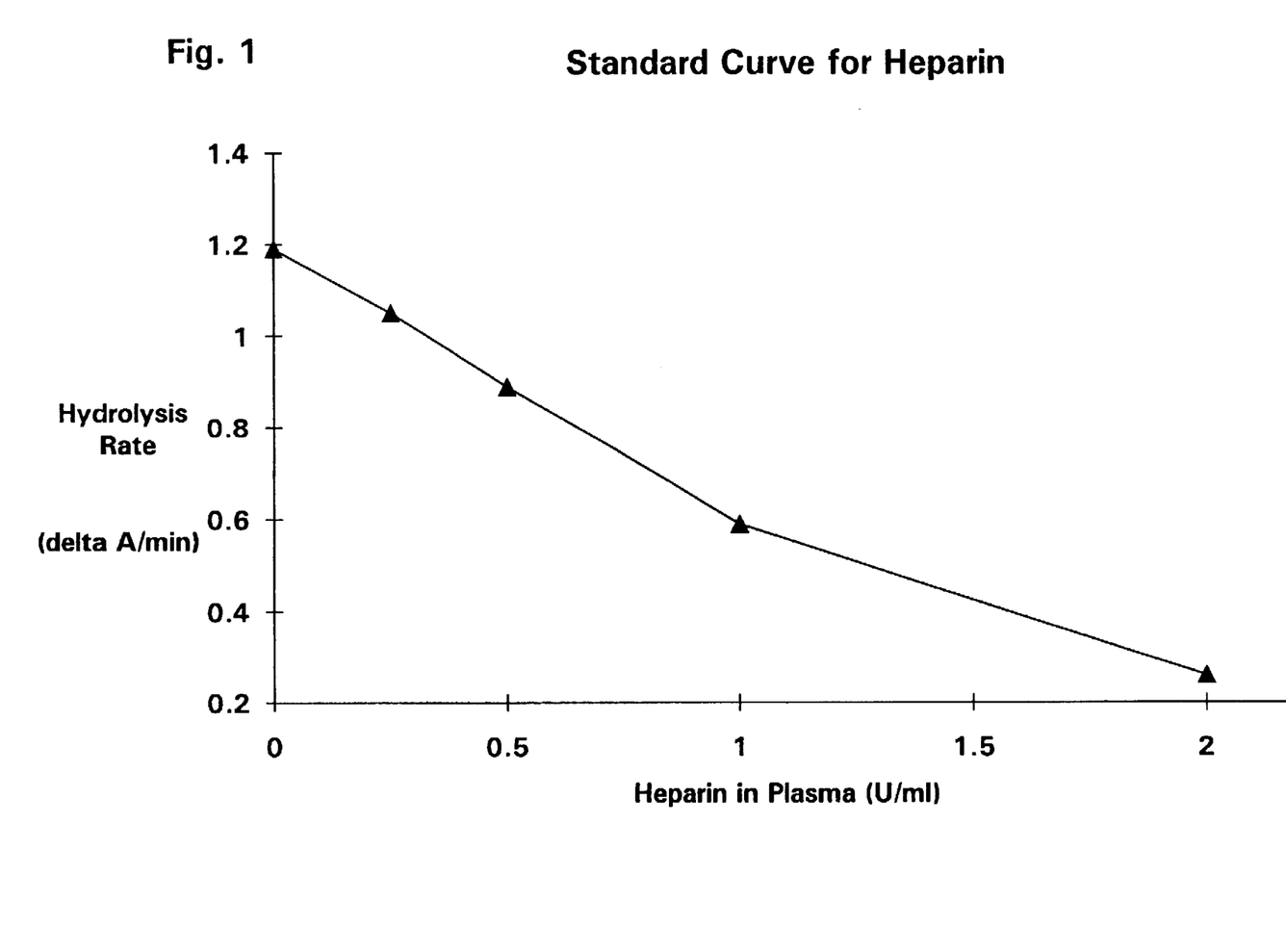
FIG. 1 shows a heparin standard curve.

200 µl of a mixture of clotting factor reagent, as described above, was combined with 100 µl of plasma which was prediluted 1 in 100 with physiological common salt solution. The reaction was started by addition of 200 µl of activator reagent as described above, and the mixture was incubated at 37° C. for 5 minutes. Then a solution of 200 µl detection reagent, as described above, was added. The amount of thrombin formed was measured on the spectral photometer at 405 nm. Previously a known amount of heparin (Liquemin™, Hoffman-LaRoche, Basel) was added to plasma and the dose response curve in FIG. 1 was obtained.

TABLE 1

| Heparin in plasma (U/ml) | Hydrolysis rates (ΔA/min) |
| --- | --- |
| 0 | 1.19 |
| 0.25 | 1.05 |
| 0.5 | 0.89 |
| 1 | 0.59 |
| 2 | 0.26 |

The hydrolysis rate, which is a measure for the amount of thrombin, was inhibited 50% when 1 U/ml heparin was present in the undiluted plasma sample. To verify the validity of the test plasma of a patient receiving heparin was tested in two ways. First, it was determined with the classical APTT-test: a clotting time of 55.1 seconds was found. This value corresponds to 0.91 U/ml of heparin. Second, patients's plasma was diluted 100 times and measured in the chromogenic assay. A hydrolysis rate of 0.662 A/min was found, which corresponds to 0.89 U/ml of heparin (see FIG. 1).

EXAMPLE 2

Determination of Low-Molecular Heparins

The chromogenic substrate method shown in Example 1 was used to determine the amount of low-molecular weight heparin (Fragmin™, Kabi, Munich) in plasma. Plasma diluted 100-fold with physiological salt was combined with the indicated amounts of FRAGMIN™ (Kabi, Munich). These samples were tested in the same way as described in Example 1.

TABLE 2

| Low Molecular Weight Heparin in Plasma (Anti $FX_a$ units) | Hydrolysis rates ($\Delta A$/min) |
|---|---|
| 0 | 1.0 |
| 1.25 | 0.9 |
| 2.5 | 0.77 |
| 5 | 0.58 |
| 10 | 0.37 |

Figure 2:
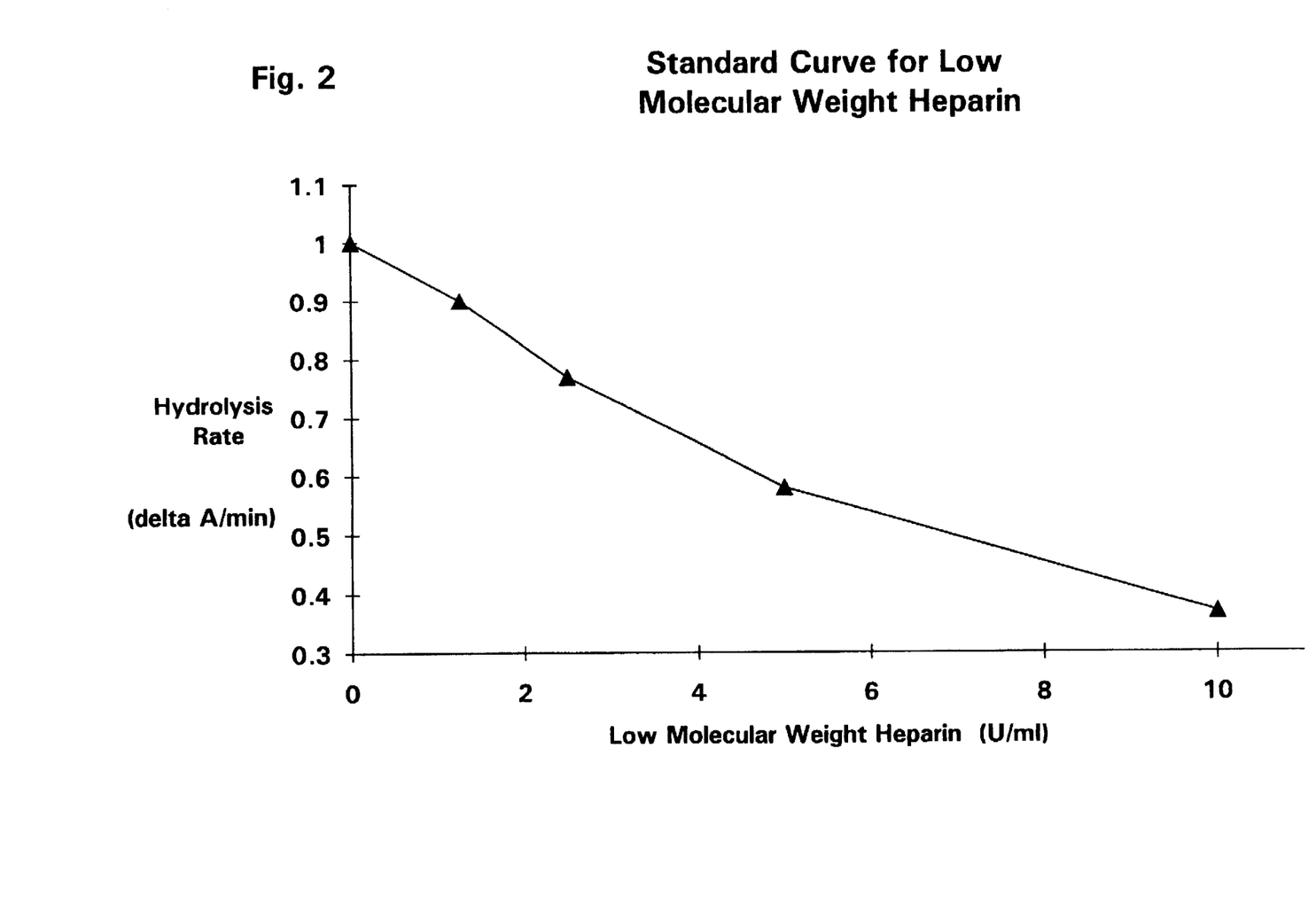
FIG. 2 shows a standard curve for low molecular weight heparin.

It was found that Thrombin formation was inhibited 50% when six anti $FX_a$ units (U/ml) of low-molecular weight heparin are present per ml of plasma sample. See FIG. 2.

EXAMPLE 3

Determination of Hirudin

Figure 3:
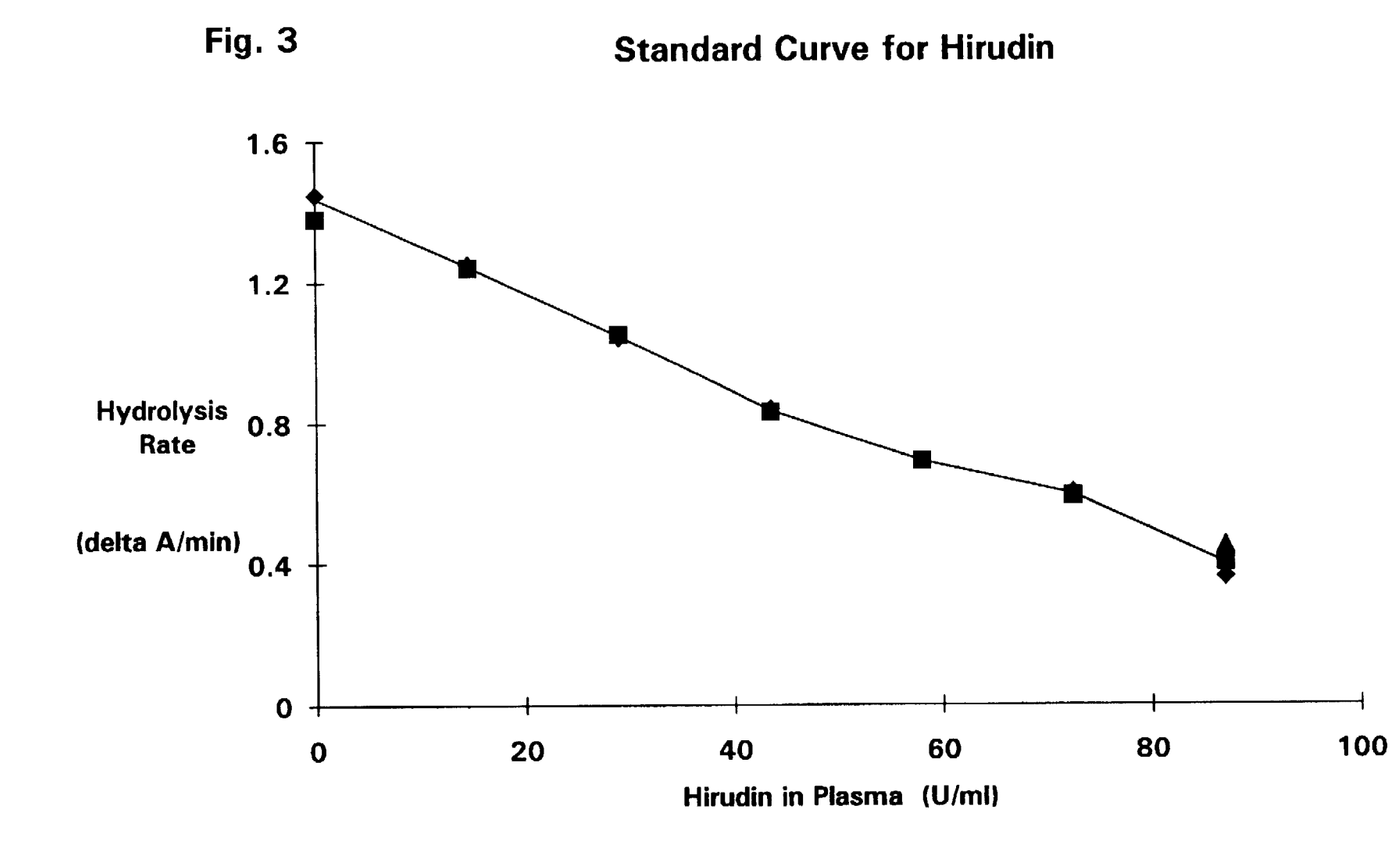
FIG. 3 shows a hirudin standard curve.

For the determination of hirudin, plasma samples were prepared with increasing amounts of hirudin (Sigma Biochemicals, St. Louis). The plasma samples were diluted 100-fold with a physiological salt solution and tested as described in Example 1. The thrombin formation is inhibited 50% when 50 U/ml hirudin is present in the plasma. See FIG. 3.

TABLE 3

| Hirudin in Plasma (U/ml) | Hydrolysis rates ($\Delta A$/min) | |
|---|---|---|
| 0 | 1.45 | 1.44 |
| 14.5 | 1.25 | 1.24 |
| 29 | 1.04 | 1.05 |
| 43.5 | 0.84 | 0.83 |
| 58 | 0.69 | 0.69 |
| 72.5 | 0.60 | 0.59 |
| 87 | 0.36 | 0.41 |

EXAMPLE 4

Determination of Heparin with a Fixed Absorbance Technique

To simplify the determination (dispensing with a pipetting step) a chromogenic substrate (CHROMOZYM TH™, Boehringer, Mannheim) was added in a concentration of 70 µM to a modified clotting factor reagent. 400 µl of this reagent was mixed with 100 µl of ten times diluted plasma sample containing a known amount of heparin. The reaction was started by addition of 200 µl of a modified activator reagent.

Clotting Factor Reagent:

50 nM factor X, 1.25 nM factor VIII, 125 nM prothrombin, 2.5 nM factor V, 125 nM antithrombin III, 15 µM phospholipids, 0.1 mM $CaCl_2$, 20 mg/ml albumin, 70 µM CHROMOZYM TH™, Boehringer Mannheim.

Activator Reagent:

2.5 nM factor $IX_a$, 15 mM CaCl2, 0.5 mg/ml albumin.

The liberation of paranitroaniline from the chromogenic substrate was followed photometrically and the time was determined in which an extinction increase of 0.1 (absorption units) was reached.

TABLE 4

| Reaction time (minutes) | Hydryolsis rates ($\Delta A$/min) | | | using plasma with 0 U/ml heparin |
|---|---|---|---|---|
| | 0.5 | 0.25 | 0.125 | |
| 0 | 0.09 | 0.1 | 0.09 | 0.092 |
| 0.5 | 0.09 | 0.102 | 0.092 | 0.094 |
| 1 | 0.092 | 0.105 | 0.166 | 0.268 |
| 1.5 | 0.103 | 0.139 | 0.437 | 0.436 |
| 2 | 0.131 | 0.274 | 0.451 | 0.44 |
| 2.5 | 0.181 | 0.407 | 0.455 | 0.44 |
| 3 | 0.261 | 0.425 | 0.455 | 0.44 |
| 3.5 | 0.354 | 0.43 | 0.456 | 0.44 |
| 4 | 0.416 | 0.43 | 0.456 | 0.441 |
| 4.5 | 0.428 | 0.434 | 0.457 | 0.441 |
| 5 | 0.43 | 0.434 | 0.457 | 0.441 |

Figure 4:
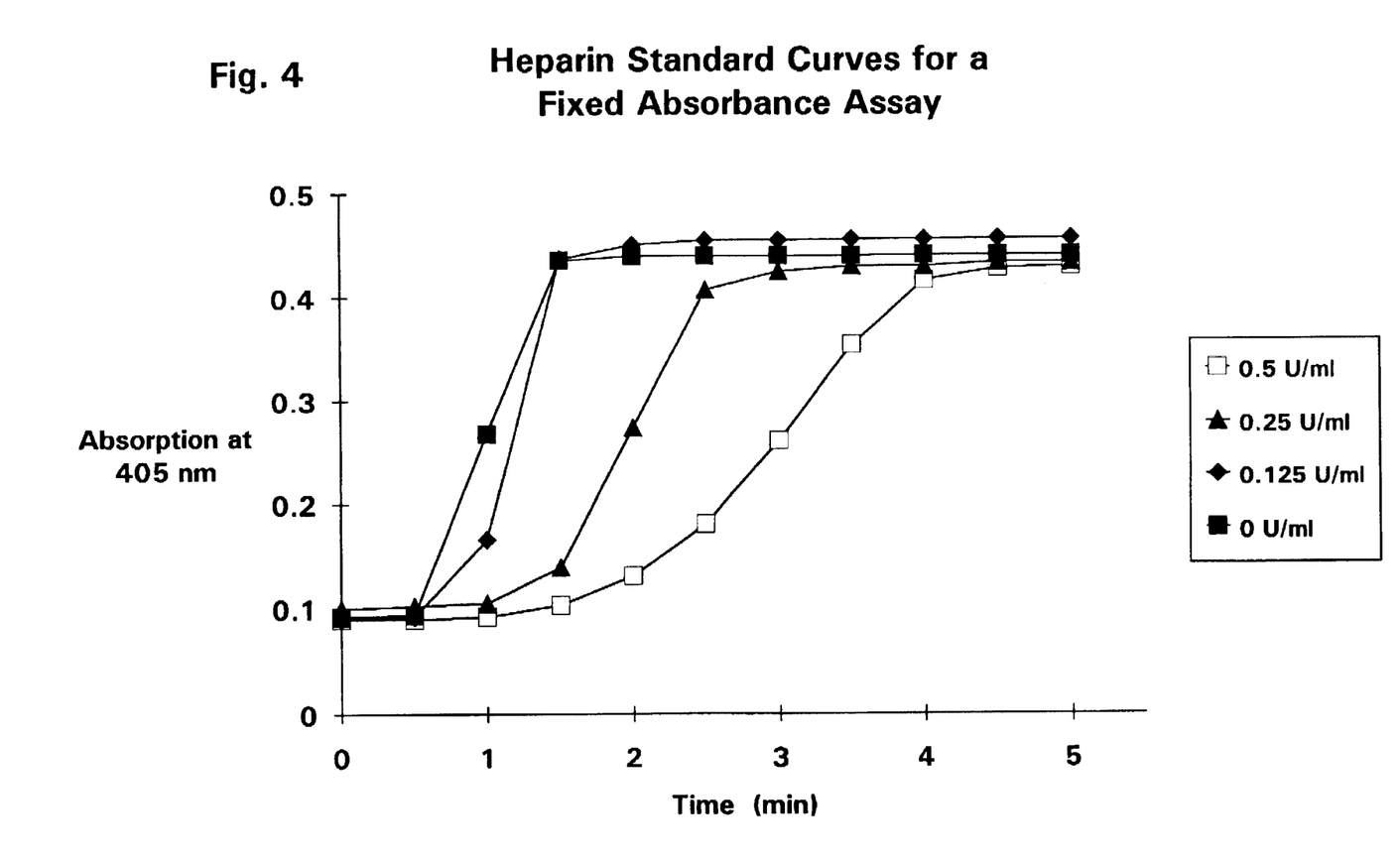
FIG. 4 shows a heparin standard curve for a fixed absorbance assay.

FIG. 4 shows that the time to reach an absorption increase of 0.1 is dependent on the amount of heparin present in the plasma.

EXAMPLE 5

Determination of Heparin in the Coagulation Assay

Figure 5:
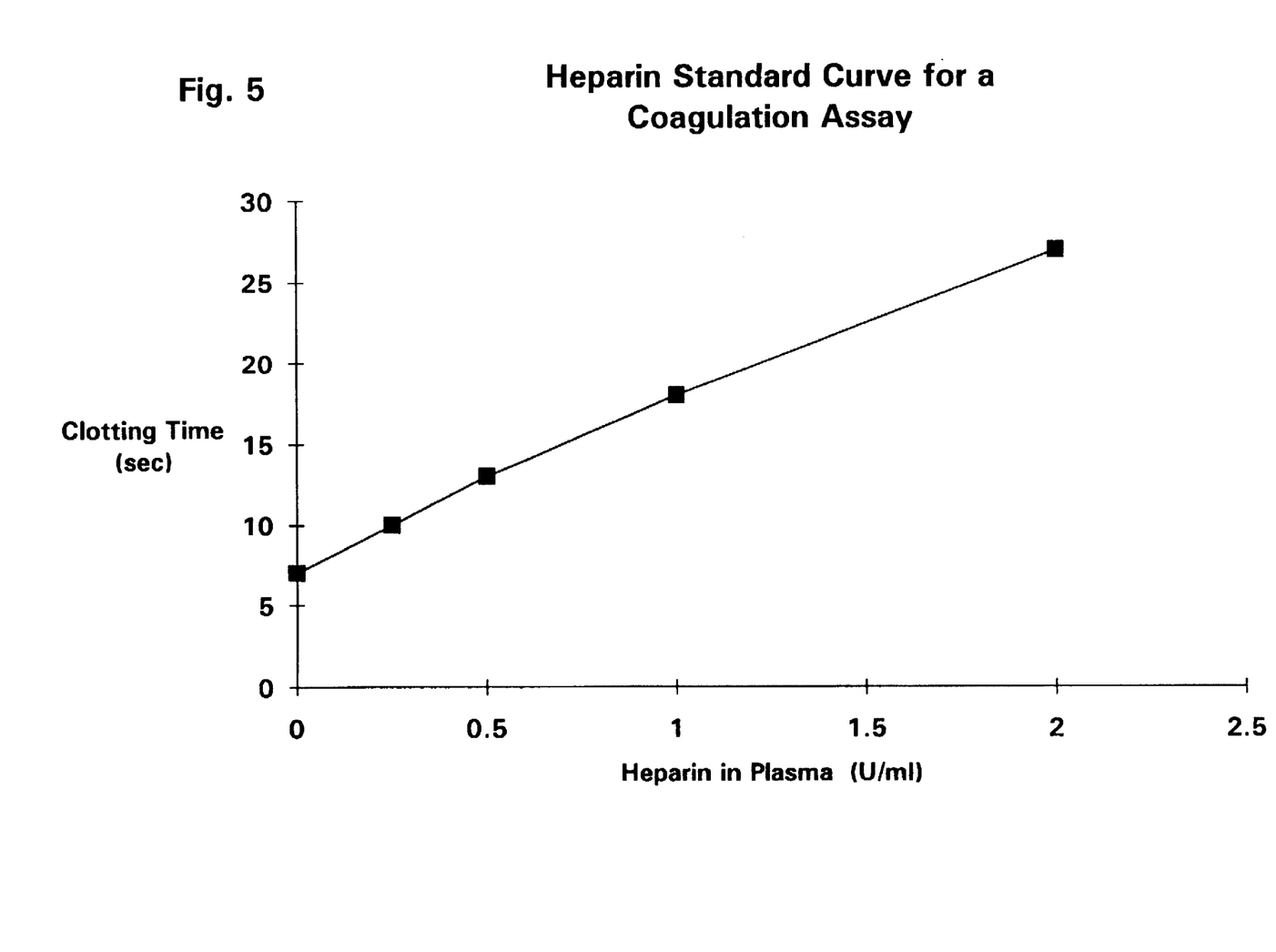
FIG. 5 shows a heparin standard curve for a clotting assay.

Clotting factor and coagulation cascade initiator reagents described in Example 1 can be used likewise for the determination of heparin using a coagulation test. In this example, a solution of fibrinogen (Kabi) in a concentration of 5 mg/ml is used. Plasma samples containing an increasing amount of heparin were prepared and diluted ten times in a physiological salt solution. To measure heparin in the samples, 100 µl sample was mixed with 100 µl of clotting factor reagent. The reaction was initiated by addition of 100 µl activator reagent and after five minutes incubation at 37° C. 100 µl of fibrinogen was added to the solution and the clotting time was measured. A dose response curve was obtained showing increased coagulation time as more heparin is present in the plasma sample. See FIG. 5.

TABLE 5

| Heparin in plasma (U/ml) | Clotting Times (Seconds) |
|---|---|
| 0 | 7 |
| 0.25 | 10 |
| 0.5 | 13 |
| 1 | 18 |
| 2 | 27 |

EXAMPLE 6

Determination of Heparin in Whole Blood

Figure 6:
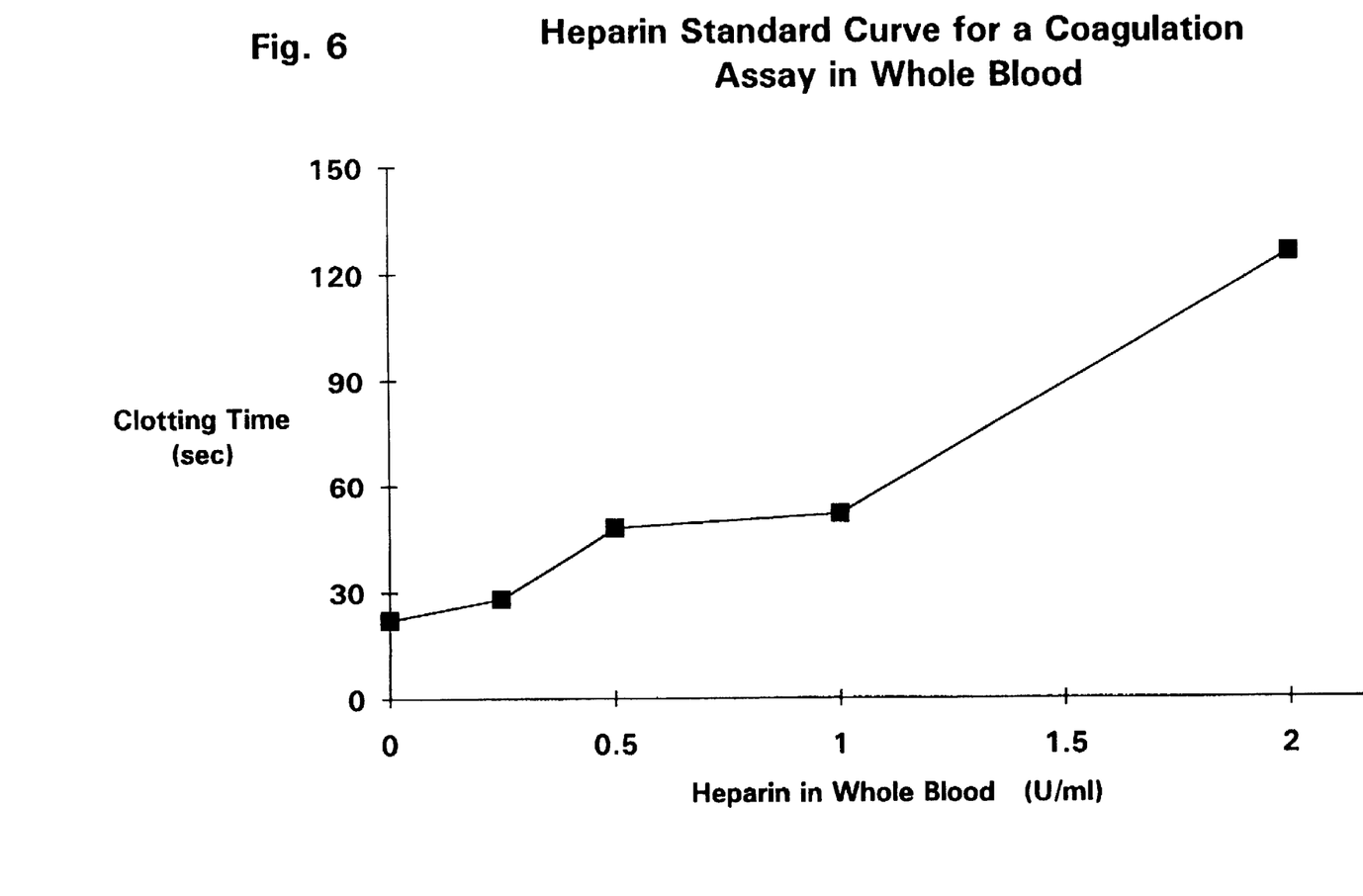
FIG. 6 shows a heparin standard curve for a clotting assay in whole blood.

Samples of citrated whole blood were prepared with increasing amounts of heparin (LIQUEMIN™, Hoffman- LaRoche). These samples were diluted ten times in a physiological salt solution and tested in the same was as described in Example 5. The measurement of the coagulation time was made with the aid of the manual hook technique (Hiaekeltechnik) according to Koller. Here, also, a dose responsive curve was found. See FIG. 6.

TABLE 6

| Heparin in blood (U/ml) | Clotting times (seconds) |
|---|---|
| 0 | 22 |
| 0.25 | 28 |
| 0.5 | 48 |
| 1 | 52 |
| 2 | 126 |

EXAMPLE 7

Determination of α-NAPAP

Figure 7:
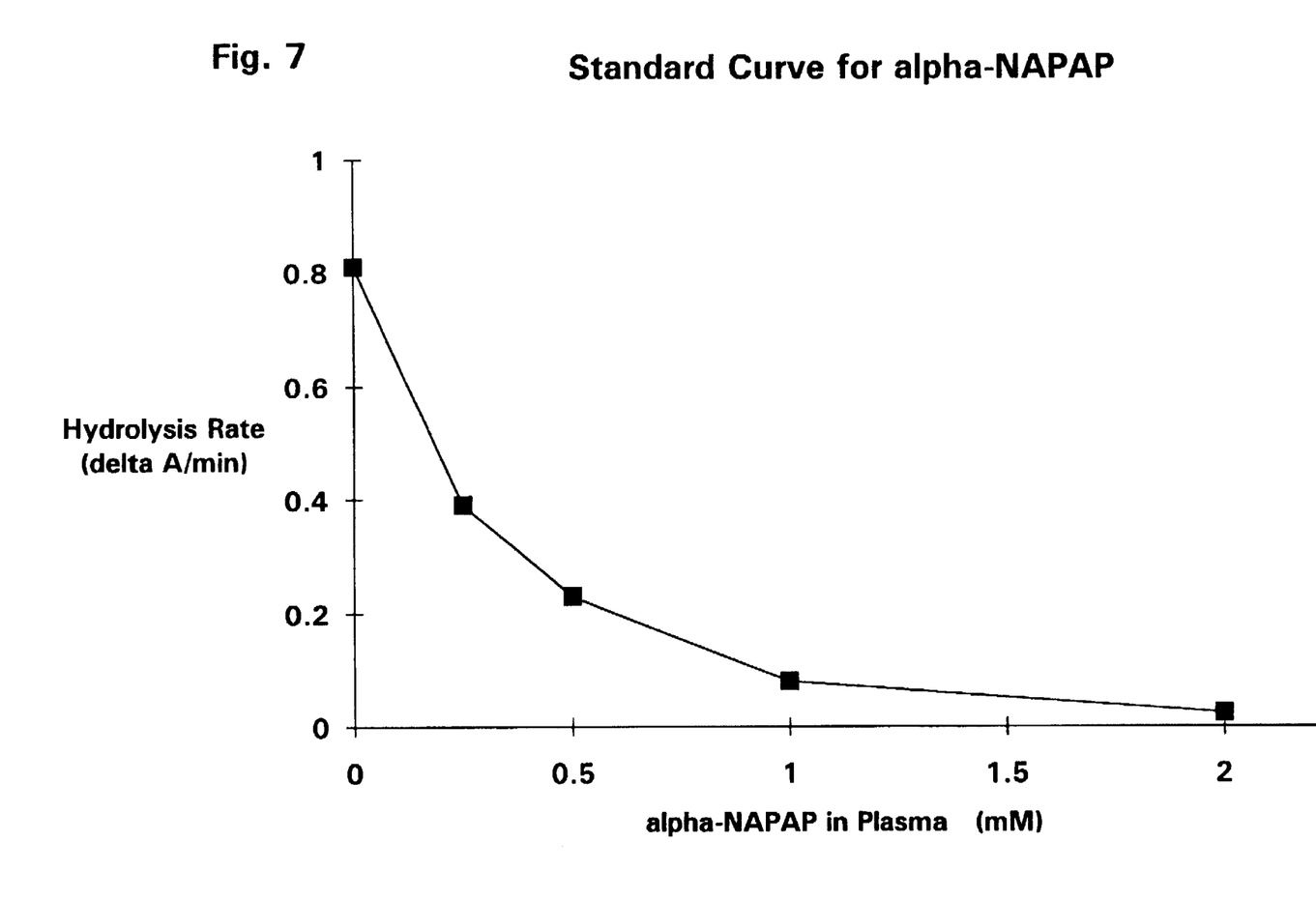
FIG. 7 shows an α-NAPAP standard curve.

For the determination of α-NAPAP (N α(-Naphthalenesulphonyl-glycyl)-4-amidino-DL-phenylalaninepiperidide, Sigma Biochemicals, St. Louis) plasma samples were prepared with increasing amounts of α-NAPAP and a test was carried out in the same way of Example 1. The following response curve was obtained. See FIG. 7.

TABLE 7

| α-NAPAP in plasma (mM) | Hydrolysis rates (ΔA/min) |
|---|---|
| 0 | 0.81 |
| 0.25 | 0.39 |
| 0.5 | 0.23 |
| 1 | 0.08 |
| 2 | 0.024 |

EXAMPLE 8

Determination of Dermatan Sulphate

Figure 8:
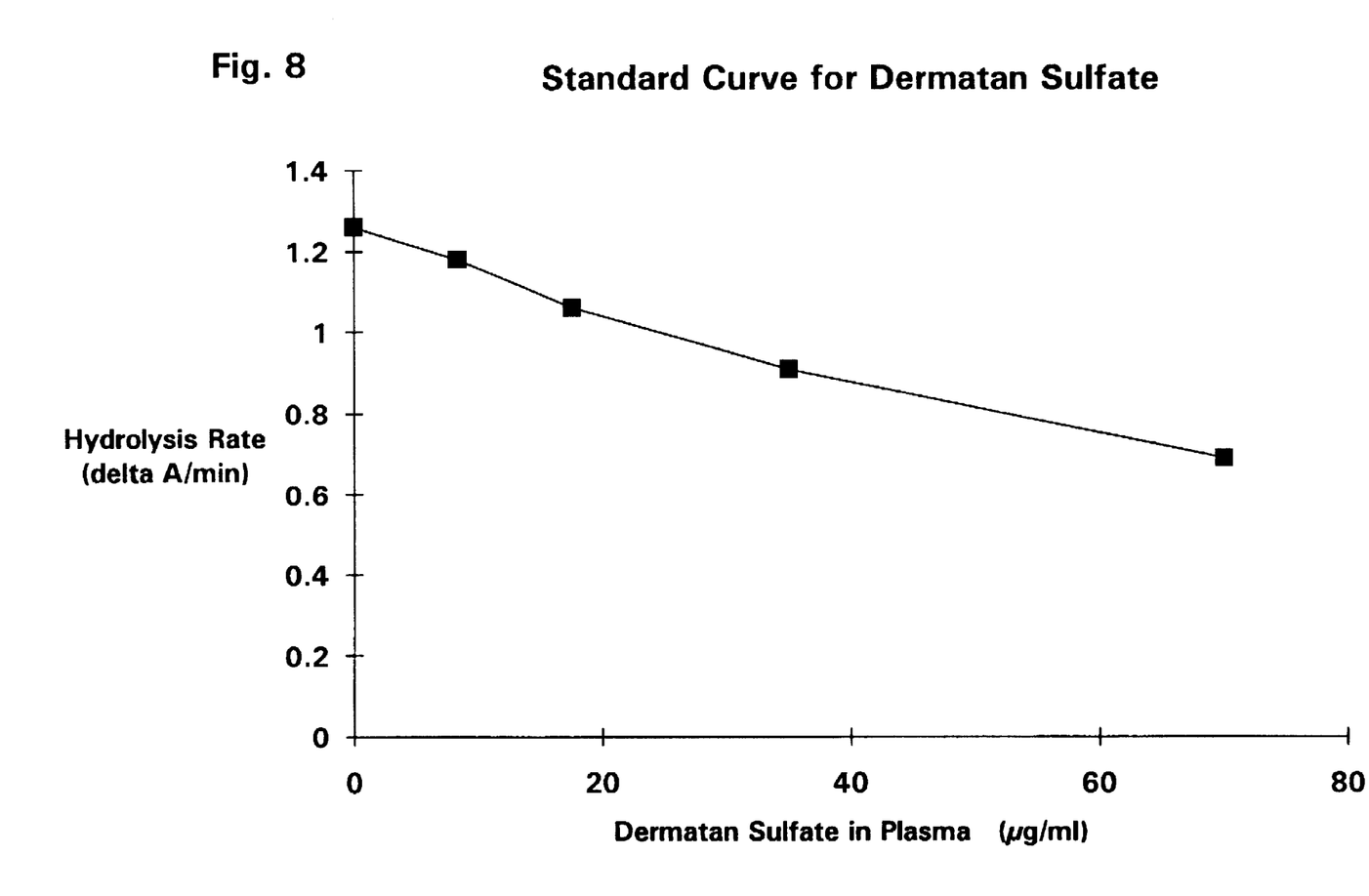
FIG. 8 shows a standard curve for dermatan sulphate.

For the determination of dermatan sulphate (Sigma Biochemicals, St. Louis) clotting factor reagent, described in Example 1, was modified: antithrombin III was replaced by heparin cofactor II (140 nM) (Diagnostica Stago, France). Plasma samples were prepared with increasing amounts of dermatan sulphate and a test was carried in the same way of Example 1. Here a dose response curve was obtained. See FIG. 8.

TABLE 8

| Dermatan Sulphate in Plasma (μg/ml) | Hydrolysis Rates (ΔA/min) |
|---|---|
| 0 | 1.26 |
| 8.25 | 1.18 |
| 17.5 | 1.06 |
| 35 | 0.91 |
| 70 | 0.69 |

It should be understood that the specification and examples are illustrative, but not limitative of the present invention and other embodiments with the spirit and scope of the invention will suggest themselves to those skilled in the art.

What is claimed is:

1. A method to determine a concentration of an anticoagulant in a sample as a function of thrombin formation in said sample comprising:
   (a) combining said sample with an amount of clotting factor reagent comprising prothrombin wherein the amount of clotting factor reagent is in excess of an amount of clotting factor present in a normal sample and is sufficient to initiate thrombin formation in said sample;
   (b) adding a sufficient amount of activator reagent to initiate coagulation;
   (c) adding a sufficient amount of a thrombin substrate to detect thrombin formation;
   (d) measuring thrombin formation; and
   (e) determining the amount of said anticoagulant in said sample by correlating the thrombin formation in said sample with thrombin formation in samples containing known amounts of said anticoagulant.

2. The method of claim 1 wherein said clotting factor reagent is comprised of clotting factor in excess, a sufficient amount of calcium ions to stabilize said clotting factor, a sufficient amount of phospholipids to catalyze the coagulation cascade reaction, and a sufficient amount of weak thrombin inhibitor to suppress thrombin formation in said sample.

3. The method of claim 2 wherein said anticoagulant is selected from the group consisting of: heparin, α-NAPAP and dermatan sulfate and the clotting factor reagent also comprises a sufficient amount of dextran sulfate to neutralize platelet factor 4 in said sample when the anticoagulant is heparin.

4. The method of claim 3 wherein said weak thrombin inhibitor is selected from the group consisting of antithrombin III, heparin cofactor II or a synthetic physiological inhibitor of thrombin which is potentiated by an anticoagulant.

5. The method of claim 1 wherein said clotting factor reagent is comprised of clotting factor in excess, a sufficient amount of calcium ions to stabilize said clotting factors, and a sufficient amount of phospholipids to catalyze the coagulation cascade reaction.

6. The method of claim 5 wherein said anticoagulant is selected from the group consisting of hirudin and synthetic physiological inhibitors of thrombin.

7. The method of claim 1 wherein the clotting factor reagent further comprises: Factor X, Factor VIII, Factor V, Factor IX or Factor IX–Factor XI complex.

8. The method of claim 1 wherein said activator reagent comprises a sufficient amount of Factor IXa, and $CaCl_2$.

9. The method of claim 1 wherein said thrombin substrate is chromogenic, luminogenic, fluorogenic or electrogenic.

10. The method of claim 1 wherein said thrombin substrate is a fibrogenic solution.

11. A method to determine a presence or concentration of an anti-coagulant in a sample, the method comprising:
   a) combining the sample with a clotting factor reagent comprising prothrombin wherein the prothrombin is added in an amount in excess of amounts present in normal samples, an activator of coagulation in an amount sufficient to initiate coagulation, and a thrombin substrate;
   b) measuring thrombin formation; and c) determining the presence or concentration of the anti-coagulant by correlating thrombin formation of the sample with thrombin formation of samples containing known concentrations of said anti-coagulant.

12. A kit to determine a concentration of an anticoagulant in a sample comprising:
   a. a first vessel containing a clotting factor reagent comprising prothrombin wherein clotting factors are in excess of a concentration of said clotting factors present in a normal sample;
   b. a second vessel containing an activator reagent; and
   c. a third vessel containing a thrombin substrate.

13. A kit to determine a concentration of an anticoagulant in a sample comprising:
   a. a first vessel containing a clotting factor reagent comprising prothrombin wherein clotting factors are in excess of a concentration of said clotting factors present in a normal sample and a thrombin substrate; and
   b. a second vessel containing an activator reagent.

* * * * *